(12) United States Patent
Solomon

(10) Patent No.: US 7,303,097 B2
(45) Date of Patent: Dec. 4, 2007

(54) SURFACE TREATMENT ARTICLES AND METHODS

(76) Inventor: Sandra R. H. Solomon, 2521 E. San Miguel Ave., Phoenix, AZ (US) 85016

( * ) Notice: Subject to any disclaimer, the term of this patent is extended or adjusted under 35 U.S.C. 154(b) by 430 days.

(21) Appl. No.: 11/037,712

(22) Filed: Jan. 18, 2005

(65) Prior Publication Data
US 2006/0157513 A1  Jul. 20, 2006

(51) Int. Cl.
*B67D 1/07* (2006.01)
(52) U.S. Cl. ........................ 222/192; 401/197
(58) Field of Classification Search .......... 222/192, 222/190, 191, 634; 401/197, 218–220, 21, 401/23, 208; 15/248.2, 230.11
See application file for complete search history.

(56) References Cited

U.S. PATENT DOCUMENTS

| | | | | |
|---|---|---|---|---|
| 2,325,867 A | * | 8/1943 | Matsakas | 401/197 |
| 2,708,763 A | * | 5/1955 | Jacoby | 401/194 |
| 3,877,823 A | * | 4/1975 | Leland | 401/197 |
| 4,032,238 A | * | 6/1977 | Leland | 401/195 |
| 5,887,759 A | * | 3/1999 | Ayigbe | 222/192 |
| 6,877,925 B2 | * | 4/2005 | Fernandez | 401/197 |

* cited by examiner

*Primary Examiner*—Lien M. Ngo
(74) *Attorney, Agent, or Firm*—Janine Rickman Novatt; Jeffrey Weiss; Weiss & Moy, P.C.

(57) ABSTRACT

A surface treatment dispenser is provided for substantially eliminating potentially harmful surface contaminants. The dispenser includes a handle coupled to a pair of nesting roller members each having a plurality of openings with one roller member being rotatable between a position where the plurality of apertures are aligned to allow the flow of decontaminant from within the inner nesting roller member and where the plurality of apertures are not aligned to prevent the flow of decontaminant. The device may also include a fine mesh cylinder within the inner nesting roller member to substantially prevent soaking the surface with decontaminant and a storage sleeve. Other decontamination devices are also provided that includes a container of decontaminant with a removable applicator in fluid communication with the contents of the container and a wipe containing decontaminant.

14 Claims, 5 Drawing Sheets

SURFACE TREATMENT ARTICLES AND METHODS

FIELD OF THE INVENTION

The present invention relates generally to decontamination devices and methods. More specifically, this invention relates to surface treatment articles and methods that may be used to substantially eliminate surface contaminants.

BACKGROUND OF THE INVENTION

The dangers of some contaminants are well known and have caused pandemics and death throughout history. In addition, they can create quality of life issues, for example, in allergy sufferers and in people with weakened immune systems. In today's mobile society, people are especially concerned about unfamiliar contaminants from across the world. For the purposes of this invention, a "contaminant" refers to that which on coming into contact with a surface will make it impure, unclean, or unfit and includes, but is not limited to, allergens, fungi, and bacteria. Some contaminants are harmful, while others are just undesirable. Contaminants may include, but are not limited to, those that are airborne and come in contact with a surface. A "decontaminant" is an agent that is substantially effective at cleaning, disinfecting, etc. the surfaces to at least temporarily eliminate contaminants.

An individual contaminates and is exposed to contaminants throughout the course of a day every time he or she touches or otherwise contacts a surface and every time someone around that person coughs or sneezes. An animal may also contaminate a surface. Once one surface is contaminated, cross-contamination onto other surfaces is all too common. Contaminants on surfaces, especially fabric surfaces, in addition to any health concerns, may also cause odors, stains, and deterioration of the surface.

As a result, people are concerned with eliminating contaminants. These concerns have caused the proliferation of decontaminants such as antibacterial soaps and cleansers. While contaminants can be easily removed from skin by washing the exposed area, the removal of contaminants from fabric surfaces is not so easy. Thorough cleaning of loose fabric surfaces typically requires machine washing or dry cleaning. Cleaning of fixed fabric surfaces such as on furniture usually requires the use of specialized equipment by specialists. These processes are time-consuming, inconvenient, and may be impractical on a regular basis. In addition, frequent washings cause overall deterioration of the fabric. For example, it is especially impractical to wash bulky coats, bedspreads, furniture coverings or the like on a daily basis yet these articles are exposed to contaminants on a regular basis, especially those used in a public venue such as a hospital, nursing home, train, restaurant, hotel, airplane, or the like. Even when dry cleaned or washed in a public venue, cross-contamination from the dry cleaners or public venue may occur.

Accordingly, there exists a need for novel devices and methods that are easy to use, portable, convenient, relatively quick, substantially safe for fabrics and effective at eliminating contaminants, relatively inexpensive, can treat a substantially large surface area with uniform application. The present invention fulfills these needs and provides further related advantages.

SUMMARY OF THE INVENTION

According to the present invention and exemplary embodiments thereof described herein, decontamination devices are provided for use in substantially eliminating contaminants on fabric surfaces in a quick and easy manner. In a first preferred embodiment, the decontamination device comprises a surface treatment dispenser. The surface treatment dispenser generally comprises an elongated handle coupled to a roller member including nesting outer and inner roller members each having a plurality of apertures, one of the outer and inner roller members being rotatable to cover and uncover said plurality of apertures in the inner roller member to alternately prevent and permit flow of decontaminant from inside the inner roller member to the surface. The roller member may further include a mesh cylinder inside the inner roller member and may be stored within a removable sleeve.

The inner roller member includes a first end and a second end. The first end is closed so as to form a container for the decontaminant. The inner roller member first end may be closed by a removable endcap.

The outer roller member also includes a first and second end. The outer roller member first end may include a primary series of threads on the inboard surface to engage with the second series of threads on the outboard surface of the inner roller member second end to act as a rotation stop.

The surface treatment dispenser may be refilled with decontaminant by removing the handle and then replacing the handle after refilling. Alternatively, the dispenser may be refilled by removing and then replacing the endcap after filling the inner roller member.

The method of using a surface treatment dispenser on a contaminated surface is also provided and comprises the steps of:

Providing a surface treatment dispenser comprising a handle coupled to a roller member defined by an inner roller member containing decontaminant and nested in an outer roller member each having a plurality of apertures;

Twisting the outer roller member to align the plurality of apertures in the outer roller member with the plurality of apertures in the inner roller member to permit the flow of decontaminant from inside the inner roller member; and Rolling the surface treatment dispenser with a slight pressure against the contaminated surface to expel decontaminant from inside the inner roller member. The decontaminant is delivered in a controlled sparing dose so as not to soak the article.

In alternative embodiments, the decontaminant may also be delivered in a controlled sparing dose from a container through a removable applicator in fluid communication with the contents of the container. The container may further include a removable overcap. The removable applicators may include a mesh like filter pad, dabber, roll top, aerosol, or sprayer with a fine mist setting. In another embodiment, the decontaminant may be delivered in a controlled sparing dose from a wipe containing the decontaminant.

Other features and advantages of the invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
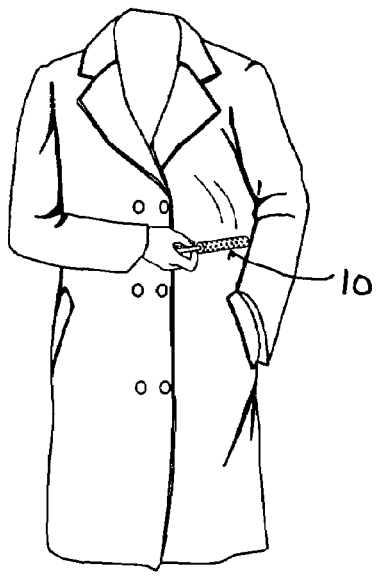
FIG. 1 is an operational perspective view of a surface treatment dispenser embodying the novel features of the invention, illustrating movement of the surface treatment dispenser over a coat.
Figure 2:
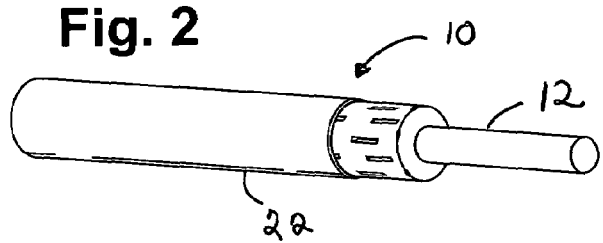
FIG. 2 is a perspective view of the surface treatment dispenser, illustrating the dispenser partially withdrawn from a removable sleeve over a roller member.

As shown in the drawings for purposes of illustration, a surface treatment dispenser referred to generally in FIGS. 1 and 2 by the reference numeral 10 is provided for substantially eliminating surface contaminants. The dispenser is specifically designed to be easy to use, portable, convenient, and substantially safe for fabrics.

Individuals are exposed to contaminants on a regular basis by contacting or otherwise touching contaminated surfaces. Fabric surfaces are particularly difficult to decontaminate on a daily basis. As a result of such contamination, individuals may become ill and the fabric surfaces may become soiled, stained, smelly, and deteriorate. The present invention provides a convenient, easy to use device for effectively treating such fabric surfaces to substantially decontaminate such surfaces.

Figure 2A:
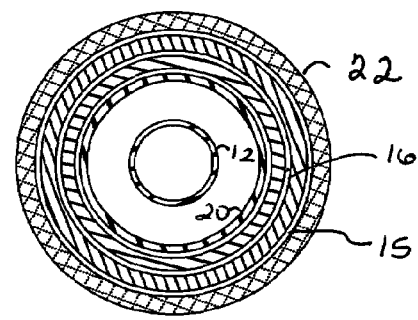
FIG. 2A is a cross-sectional view of the sleeved dispenser of FIG. 2, illustrating the removable sleeve as the outermost ring, and the dispenser including in successively decreasing diameters, an outer roller member, an inner roller member, an inner mesh cylinder and a handle.

In accordance with the present invention, and as illustrated with respect to a preferred embodiment in FIGS. 1-5, the surface treatment dispenser 10 generally comprises an elongated handle 12 coupled to a roller member 14 including nesting outer and inner roller members 15 and 16 each having a plurality of apertures 18, one of the outer and inner roller members 15 and 16 being rotatable to cover and uncover said plurality of apertures 18 in the inner roller member 16 to alternately prevent and permit flow of decontaminant from inside the inner roller member 16 to the surface. The roller member 14 may further include a mesh cylinder 20 (FIG. 4B) inside the inner roller member and may be stored within a removable sleeve 22 as shown in FIGS. 2 and 2A. As shown in 2A, the surface treatment dispenser is thus defined by generally cylindrical hollow body elements (mesh cylinder-inner roller member-outer roller member-sleeve) of successively increasing diameters, which are sized so that respective ones of said body elements are concentrically stacked.

Figure 4C:
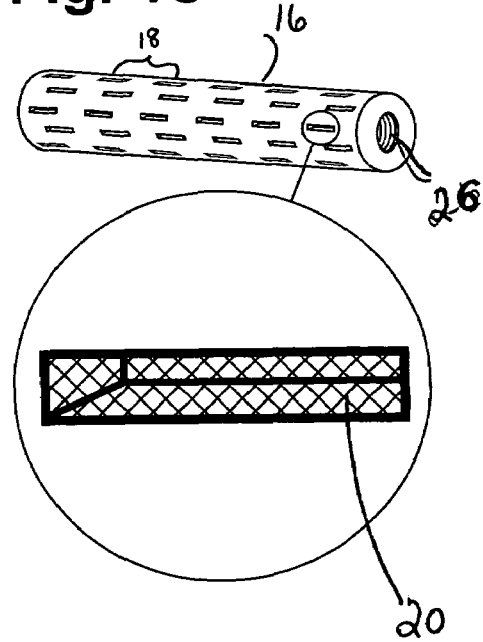
FIG. 4C is a perspective view of an exemplary inner roller member having a series of threads at a second end, illustrating in the encircled region an exploded view of the inner mesh cylinder through the plurality of apertures.
Figure 4D:
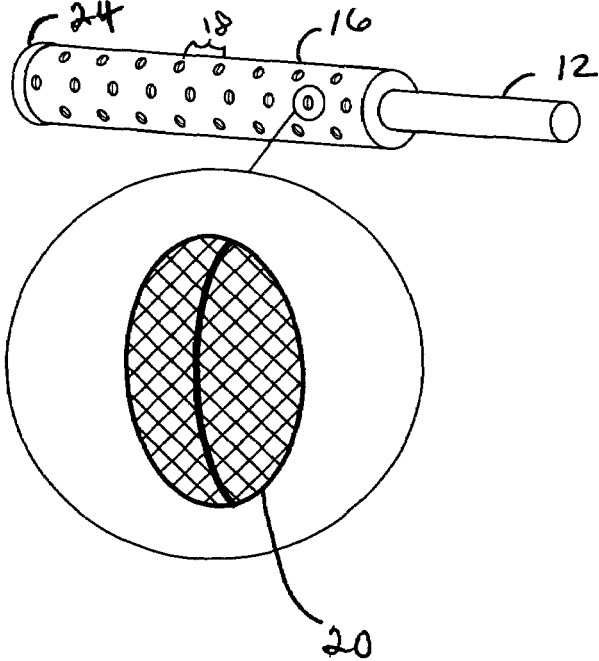
FIG. 4D is a perspective view similar to FIG. 4C of another exemplary inner roller member, illustrating a handle 12 coupled to the second end of the inner roller member and a removable refill endcap.
Figure 5:
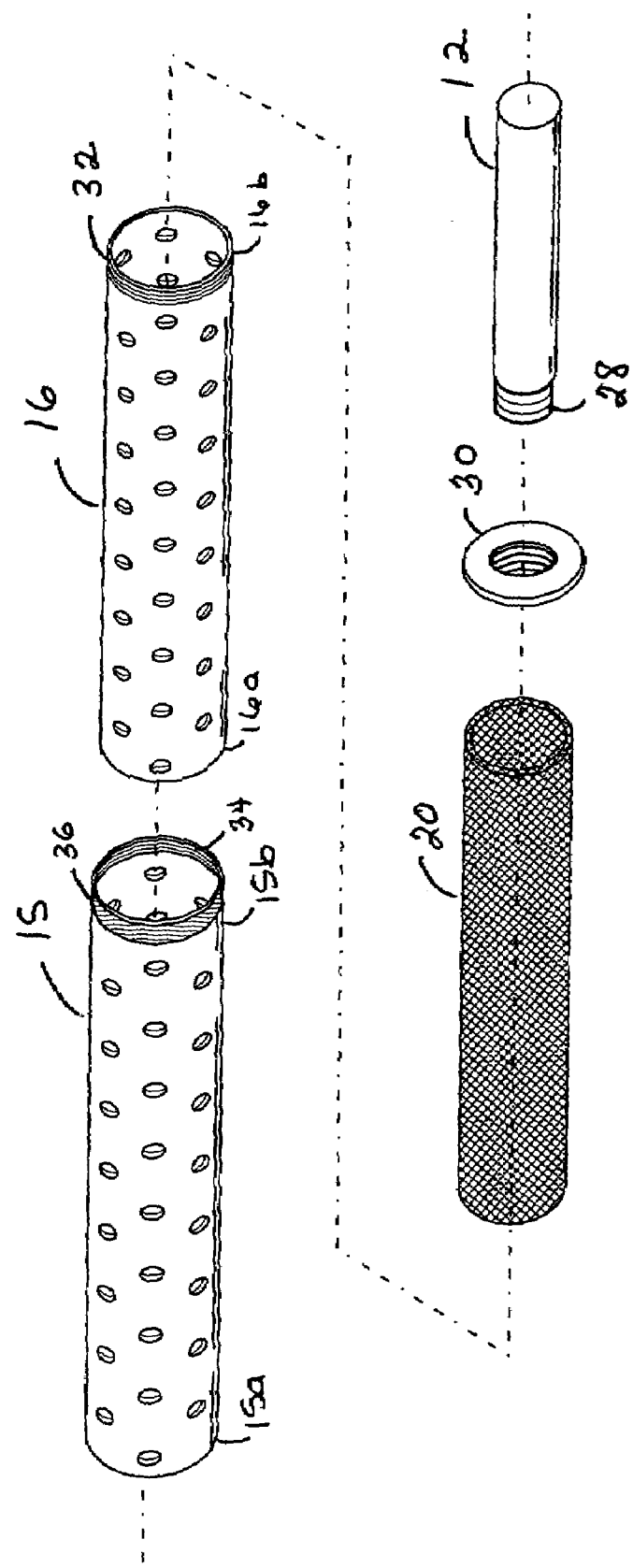
FIG. 5 is an exploded assembly view of the surface treatment dispenser.

As shown in FIG. 5, the outer and inner roller members 15 and 16 are generally hollow cylindrical tubes. The inner roller member 16 (FIGS. 4C and 4D) fits within the outer roller member 15 so that the inner cylindrical surface of the outer roller member and the outer cylindrical surface of the inner roller member are in sliding contact with each other to permit rotation of one of the outer and inner rotation members but sufficiently close so that there is substantially no seepage of decontaminant between the outer and inner roller members-when the plurality of apertures in the inner roller member are covered or uncovered.

The inner roller member 16 includes a first end and a second end 16a and 16b. The first end 16a is closed so as to form a container for the decontaminant. The inner roller member first end 16a may be closed by a removable endcap 24 (FIG. 4D). The removable endcap 24 may be a twist cap, snap cap, etc. to substantially ensure closure of the first end of the inner roller member 16. The inner roller member second end 16b may include a first series of threads 26 on its inboard surface (FIG. 4C) to engage with a series of handle threads 28 on one end of the elongated handle 12 (FIG. 5). The elongated handle 12 is normal to the middle of the inner roller member 16 and is preferably made from plastic.

Figure 3:
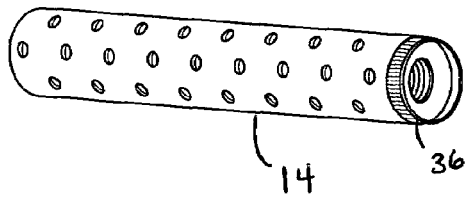
FIG. 3 is a perspective view of an exemplary roller member having an outer roller member with a knurled second end collar to reflect an inner roller member within the outer roller member, the outer and inner roller members each having a plurality of apertures in an aligned open condition.
Figure 3A:
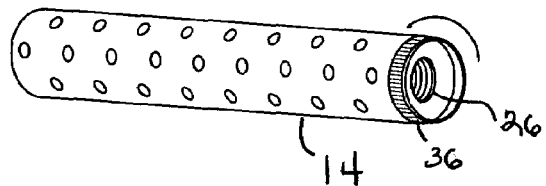
FIG. 3A is an operational perspective view of the exemplary roller member of FIG. 3, illustrating twisting movement of the outer roller member relative to the inner roller member to cover the plurality of apertures in the inner roller member.

Although the first series of threads is shown in FIGS. 3 and 3A as integral with the inner roller member 16, the inner roller member second end 16b may be fitted by any known methods with a separate threaded endpiece 30 (FIG. 5) into which the threaded end of the elongated handle 12 is received. Use of the separate threaded endpiece 30 may enable easier manufacturing of the surface treatment dispenser 10. The outboard surface of the inner roller member second end 16b may also include a second series of threads 32 for purposes as described hereinafter.

The outer roller member 15 also includes a first and second end 15a and 15b. The outer roller member first end 15a may include a primary series of threads 34 on the inboard surface to engage with the second series of threads 32 on the outboard surface of the inner roller member second end to act as a rotation stop. The outer roller member second end 15b may include a knurled collar 36 on the outboard surface of the outer roller member second end 15b to provide an improved gripping surface to enable the user to rotate the outer roller member. The outer and inner roller members 15 and 16 are preferably made of thin, pliable plastic for purposes as described hereinafter.

The plurality of apertures 18 in each of the outer and inner roller members 15 and 16 may be of any shape. Suitable shapes include, but are not limited to, rectangular apertures as shown in FIG. 4C or circular apertures as shown in FIGS. 3, 3A, 4D, and 5. In order to effectively prevent and permit flow of decontaminant, the apertures in each of the inner and outer roller members should be shaped and positioned the same vis a vis each other.

In a preferred embodiment, the outer roller member 15 rotates around the inner roller member 16 to alternately cover and uncover the plurality of apertures 18 in the inner roller member 16 to respectively permit and prevent the flow of decontaminant from inside the inner roller member 16 onto the surface. The outer roller member 15 may be rotated to and locked at the rotation stop by turning the knurled collar 36 as shown in FIG. 3A. FIG. 3 illustrates an open position of the roller member. The uncovering of the plurality of apertures can be adjusted by rotational movement of the outer roller member 15. The plurality of apertures 18 may be covered by rotating the outer roller member 15 until the plurality of apertures 18 in the inner roller member 16 are completely covered so that no apertures are aligned. It is to be understood that the inner roller member may rotate with the outer roller member stationary within the confines of this invention.

Figure 4:
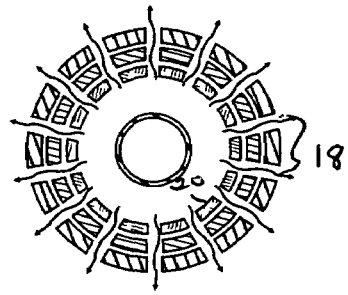
FIG. 4 is a cross-sectional view of the exemplary roller member of FIG. 3, illustrating the plurality of apertures of the outer roller member aligned with the plurality of apertures of the inner roller member to permit a decontaminant to flow out the aligned plurality of apertures.
Figure 4A:
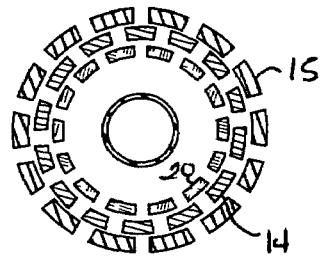
FIG. 4A is a cross-sectional view similar to FIG. 4 of the exemplary roller member of FIG. 3A, illustrating the plurality of apertures in a non-aligned position in order to substantially prevent flow of the decontaminant from inside the inner roller member.
Figure 4B:
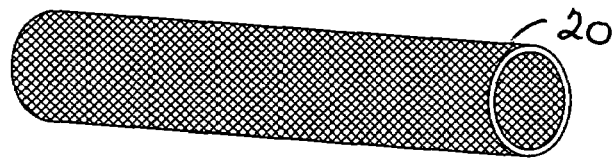
FIG. 4B is a perspective view of the inner mesh cylinder.

The roller member 14 may further include the mesh cylinder 20 shown in FIG. 4B. The mesh cylinder 20 may be press fit into the inner roller member 16. The mesh cylinder 20 is of sufficiently fine mesh such that the decontaminant does not pour out the plurality of apertures 18 in the outer and inner roller members when in the open position. The mesh cylinder 20 helps to further control the flow of decontaminant from the roller member 14 so as to substantially prevent soaking the surface with decontaminant. The mesh cylinder 20 may be preferably plastic.

The storage sleeve 22 is a cylindrical cover which snugly surrounds the exterior walls of the roller member 14. The shape of the sleeve substantially follows the outer contours of the roller member. The storage sleeve 22 may snap, slide, or twist shut over the roller member and may be removed before the dispenser is used by reversing that action. The storage sleeve 22 may be preferably plastic.

The surface treatment dispenser 10 may be refilled with decontaminant by removing the handle 12 and then replacing the handle 12 after refilling. Alternatively, the dispenser 10 may be refilled by removing and then replacing the endcap 24 (FIG. 4D) after filling the inner roller member 16. Although a refillable dispenser has been described, it is to be appreciated that a disposable dispenser is included within the confines of the invention such that the dispenser may be thrown away after depletion of the decontaminant inside the dispenser. Alternatively, the dispenser may be washed and reused.

The size of the dispenser may vary depending on its use, from a small pocket-size dispenser to a larger dispenser that may be used to treat larger surfaces. The dispenser may be constructed of pliable plastic or the like to make it lightweight and thus easy to carry as well as pliable such that pressure against the surface of the article causes the decontaminant to be expelled through the plurality of apertures 18.

The roller member 14 is manipulated by the handle 12 by rolling the dispenser 10 while applying slight pressure across the contaminated surface (e.g. a coat) as shown for example in FIG. 1. Although a manual dispenser has been described, a dispenser that is electrically operated is not to be excluded.

The method of using a surface treatment dispenser on a surface is also provided and comprises the steps of:

Providing a surface treatment dispenser comprising a handle coupled to a roller member defined by an inner roller member containing decontaminant and nested in an outer roller member each having a plurality of apertures;

Twisting the outer roller member to align the plurality of apertures in the outer roller member with the plurality of apertures in the inner roller member to permit the flow of decontaminant from inside the inner roller member; and Rolling the surface treatment dispenser with a slight pressure against the surface to expel decontaminant from inside the inner roller member. The decontaminant is delivered in a controlled sparing dose so as not to soak the article.

Figure 6:
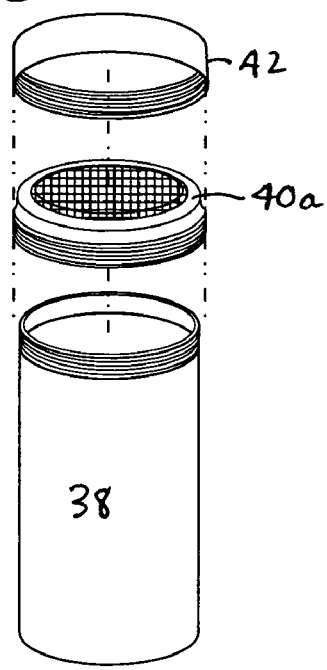
FIG. 6 is an alternative embodiment of the method of the invention, illustrating a container with a removable mesh like filter pad applicator and an overcap.
Figure 6A:
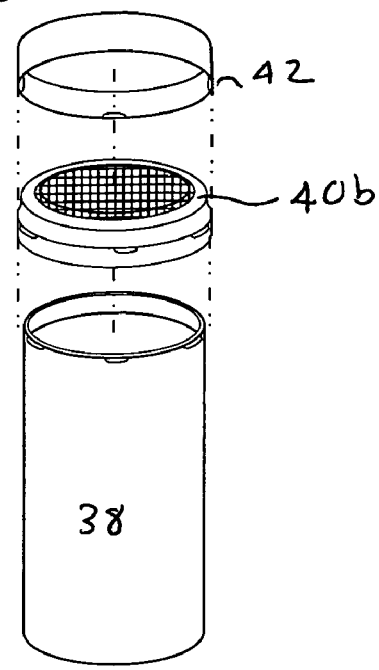
FIG. 6A is an alternative embodiment of the method of the invention, illustrating a container with a dabber applicator and an overcap.
Figure 6B:
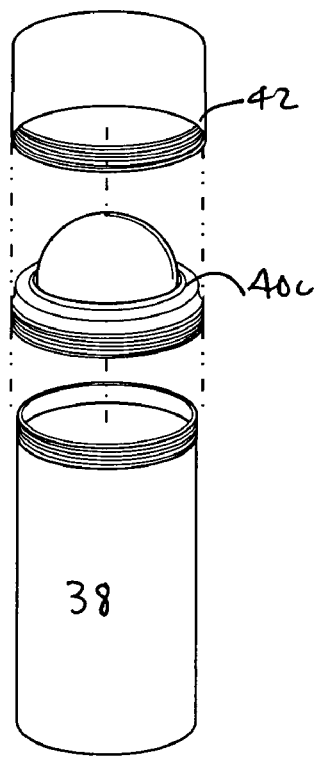
FIG. 6B is an alternative embodiment of the method of the invention, illustrating a container with a roll top applicator and an overcap.
Figure 6C:
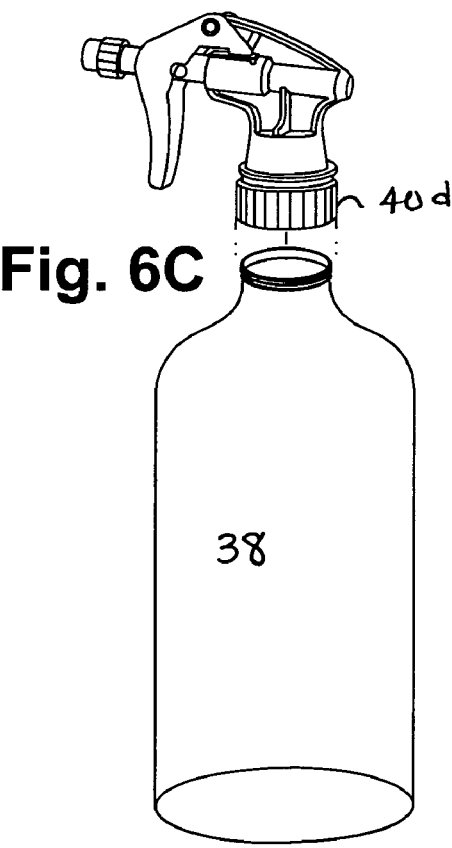
FIG. 6C is an alternative embodiment of the method of the invention, illustrating a container with a fine-mist sprayer applicator.

In alternative embodiments, as shown in FIGS. 6-6C, the decontaminant may also be delivered in a controlled sparing dose from a container 38 through a removable applicator 40a-40d in fluid communication with the contents of the container. The container may further include a removable overcap 42 to substantially prevent spillage and evaporation from the container when not in use.

The containers 38 may be of any known shape as shown in FIGS. 6-6C. The removable applicators may include a mesh like filter pad 40a made from cloth or the like (FIG. 6), dabber 40b made from cloth or the like (FIG. 6A), roll top 40c (FIG. 6B), or sprayer 40d (FIG. 6C). The decontaminant may also be delivered from an aerosol can (not shown). The containers may be refilled or discarded when the decontaminant has been depleted. The container may also be washable. The filter pad 40a shown in FIG. 6 may be replaced as necessary. The roll top 40c may be a plastic/ball like roll top. The sprayer 40d should include a setting for a fine mist so as not to soak or saturate the treated article. The dispensing applicators 40a-d may threadably engage with the container mouth, snap on, or close the container mouth by any known method.

Figure 7:
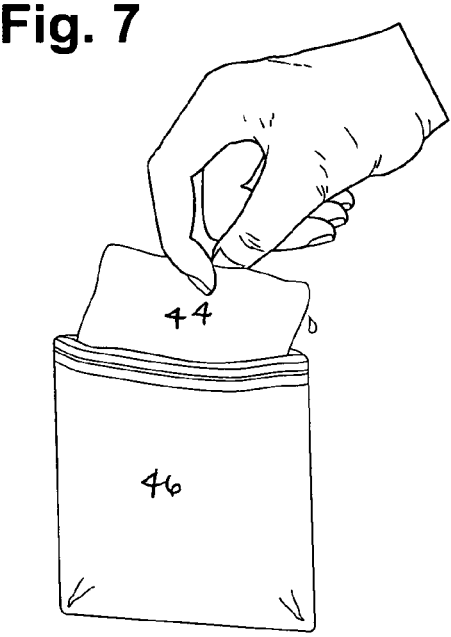
FIG. 7 is an alternative embodiment of the method of the invention, illustrating an impregnated wipe being withdrawn from a packet, illustrating a sealing strip on the packet.
Figure 7A:
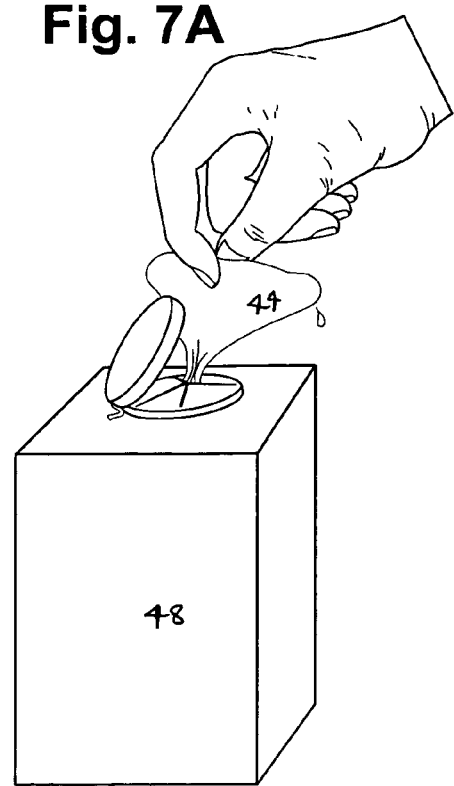
FIG. 7A is another alternative embodiment of the method of the invention, illustrating an impregnated wipe being withdrawn from a canister having a closure tab.

In another embodiment as shown in FIGS. 7 and 7A, the decontaminant may be delivered in a controlled sparing dose from a wipe 44 containing the decontaminant. As is well known in the art, a pre-moistened wipe can be any wipe, towel, tissue or sheet like product including natural fibers, synthetic fibers, synthetic material and combinations thereof, that is wet or moist or becomes wet during use or prior to use. The wipe may be saturated or otherwise impregnated with the decontaminant. The wipe may be packaged in a sealed packet 46 which is unsealed just before use (FIG. 7) or from a canister 48 (FIG. 7A) or the like that includes a closure to substantially prevent the wipe from drying out before use thereof. The wipe may be discarded after use.

The decontaminant may be selected from known decontaminants. The decontaminants may be liquid, or solid particulates. The decontaminant should be substantially safe for fabrics and dry relatively quickly if applied in liquid form. Preservatives and/or fragrances may be added to the decontaminant.

The devices and methods described herein may be used to treat contaminated surfaces including those found in the following, but not limited to: Clothing articles: jackets, overcoats, trousers, slacks, sweaters, cardigans, hats, scarves, gloves, doctor coats, uniforms, neckties, etc; Household articles: sofas, blankets, chairs, drapes, cushions, pillows, stuffed animals, dolls and doll clothing, rag books, etc.; and Commercial/Industrial articles: airplane seating, movie theaters, onstage theaters, doctor offices, hospitals, doctor and dentist waiting rooms, hotels, restaurants, automobiles, carpeting, car seats and strollers, corporate offices, universities, military, gyms, art galleries, department stores, etc.

In addition to treating already contaminated fabric surfaces, the devices and method may be used to treat fabric surfaces prior to contamination. For example, a fabric manufacturer may use the devices and method to treat its fabrics prior to being made into a particular finished article.

From the foregoing, it is to be appreciated that the above described devices and methods are substantially easy to use, portable, convenient, ready-to use, relatively quick, substantially safe for fabrics, and can treat a large surface area with substantially uniform application. The devices and methods thereby promote a healthier and cleaner environment by substantially removing undesirable and potentially harmful contaminants on everyday articles.

Although a particular embodiment of the invention has been described in detail for purposes of illustration, various modifications may be made without departing from the spirit and scope of the invention. Accordingly, the invention is not to be limited, except as by the appended claims.

I claim:

1. A surface treatment dispenser comprising in combination:
    a handle;
    a roller member coupled to the handle defining an inner roller member containing decontaminant and nested in an outer roller member each having a plurality of apertures and one of the inner and outer roller members being rotatable to cover and uncover said plurality of apertures in the inner roller member to alternately prevent and permit flow of decontaminant from inside the inner roller member to the surface through the plurality of apertures in each of the inner and outer roller members, wherein the roller member further comprises a fine mesh cylinder within the inner roller member.

2. The surface treatment dispenser of claim 1, wherein the roller member is received in a sleeve for storage.

3. The surface treatment dispenser of claim 1, wherein the inner roller member includes a removable endcap for refilling the inner roller member with decontaminant.

4. The surface treatment dispenser of claim 1, wherein the handle is removably coupled to the inner roller member for refilling the inner roller member with decontaminant.

5. The surface treatment dispenser of claim 1, further comprises means for removing the handle for refilling the inner roller member with decontaminant.

6. The surface treatment dispenser of claim 5, further comprising means for removing the handle for refilling the inner roller member with decontaminant wherein the inner roller member has a first end and a second end and the means for removing the handle define a separate threaded endpiece that fits onto the second end of the inner roller member.

7. The surface treatment dispenser of claim 6, wherein the outer roller member has a first end and a second end and the outer roller member second end includes a series of threads on an inboard surface thereof that engage with a series of threads on an outboard surface of the second end of the inner roller member to define a rotation stop.

8. The surface treatment dispenser of claim 7, wherein the outer roller member second end includes a knurled collar on an outboard surface thereof.

9. The surface treatment dispenser of claim 1, wherein the inner and outer roller members comprise generally cylindrical hollow body elements of successively increasing diameters, sized so that respective ones of said body elements are concentrically stacked.

10. A decontamination device comprising in combination:
    A first generally cylindrical roller member containing decontaminant and having a plurality of apertures;
    A second generally cylindrical roller member into which said first generally cylindrical roller member is inserted so that said second generally cylindrical roller member surrounds said first generally cylindrical roller member, said second generally cylindrical roller member having a plurality of apertures;
    Means to move the second generally cylindrical roller member in a direction perpendicular to the long axis of said first generally cylindrical member whereby the flow of decontaminant through the plurality of apertures may be controlled, wherein the decontamination device further comprises a fine mesh cylinder within the first generally cylindrical roller member.

11. The decontamination device of claim 10, wherein the decontamination device is received in a sleeve for storage.

12. The decontamination device of claim 10, further comprising a handle coupled to the first generally cylindrical roller member.

13. The surface treatment dispenser of claim 10, wherein the first generally cylindrical roller member includes a removable endcap for refilling the first generally cylindrical roller member with decontaminant.

14. The surface treatment dispenser of claim 12, wherein the handle is removably coupled to the first generally cylindrical roller member for refilling the first generally cylindrical roller member with decontaminant.

* * * * *